(12) United States Patent
Faour et al.

(10) Patent No.: US 6,491,949 B2
(45) Date of Patent: Dec. 10, 2002

(54) OSMOTIC DEVICE WITHIN AN OSMOTIC DEVICE

(75) Inventors: Joaquina Faour, Buenos Aires (AR); Marcelo A. Coppari, Buenos Aires (AR)

(73) Assignee: Osmotica Corp., Tortola (VG)

( * ) Notice: Subject to any disclaimer, the term of this patent is extended or adjusted under 35 U.S.C. 154(b) by 0 days.

(21) Appl. No.: 09/755,827

(22) Filed: Jan. 4, 2001

(65) Prior Publication Data

US 2002/0035357 A1 Mar. 21, 2002

Related U.S. Application Data

(60) Provisional application No. 60/176,081, filed on Jan. 14, 2001.

(51) Int. Cl.⁷ ................................................ A61K 9/22
(52) U.S. Cl. ........................................ 424/473; 424/468
(58) Field of Search ................................ 424/473, 468, 424/471, 472

(56) References Cited

U.S. PATENT DOCUMENTS

| | | |
|---|---|---|
| 4,111,202 A | 9/1978 | Theeuwes |
| 4,278,087 A | 7/1981 | Theeuwes |
| 4,449,983 A | 5/1984 | Cortese et al. |

*Primary Examiner*—James M. Spear
(74) *Attorney, Agent, or Firm*—Rick Matos; Innovar, L.L.C.

(57) ABSTRACT

The delivery devices described herein are capable of delivering one or more active substances by osmotic pumping through preformed passageways. An osmotic device according to the invention includes a first osmotic device enclosed within a second osmotic device. In some embodiments, the semipermeable membrane of one or both of the osmotic devices completely dissolves or degrades during use. This delivery device can include an immediate release outer coat.

55 Claims, 2 Drawing Sheets

OSMOTIC DEVICE WITHIN AN OSMOTIC DEVICE

CROSS-REFERENCE TO EARLIER FILED APPLICATION

The present application claims the priority of U.S. provisional application for patent Ser. No. 60/176,081 filed Jan. 14, 2001.

FIELD OF THE INVENTION

This invention pertains to a delivery device for the controlled release of active agents to an environment of use. More particularly, the invention pertains to a dual osmotic device for the delivery of active agents over a prolonged and extended period of time. The dual osmotic device comprises a first osmotic device enclosed within a second osmotic device.

BACKGROUND OF THE INVENTION

Osmotic devices have demonstrated utility in delivering beneficial active agents, such as medicines, nutrients, food, pesticides, herbicides, germicides, algaecides, chemical reagents, and others, to an environment of use in a controlled manner over prolonged periods of time. Known devices include tablets, pills, and capsules.

Advancements in the prior art have focused on developing osmotic devices with improved semipermeable or porous membranes, various coatings surrounding the core and/or the semipermeable membrane, layered osmotically effective agents in the core of the device, specific release profiles for specific active substances, and specific membrane or core compositions.

While the prior art discloses a wide variety of osmotic devices, none of the prior art discloses a dual osmotic device comprising a first osmotic device enclosed within a second osmotic device.

SUMMARY OF THE INVENTION

The present invention provides a dual osmotic device, which provides a controlled release device of one or more active agents, comprising a first osmotic device enclosed within a second osmotic device. The first osmotic device provides a controlled release of a first active agent through a passageway in a first semipermeable membrane. The second osmotic device provides a controlled release of a second active agent through a second passageway in a second semipermeable membrane. Both devices deliver their respective active agents through osmotic pumping. In some embodiments, the first and second passageways can be located anywhere on their respective semipermeable membranes.

According to some of the preferred embodiments of the invention, a) one or both of the first and second semipermeable membranes loses its chemical and physical integrity during use; b) the first and second active agents are the same; c) the first and second active agents are different; d) the second semipermeable membrane loses its chemical integrity after about 3–20 hours after administration; e) the second osmotic device delivers a majority of the second active agent by about 3–30 hours after administration; f) the first osmotic device delivers a majority of the first active agent after about 20 minutes after exposure to an aqueous solution; g) the second active agent is delivered to the upper to middle GI tract and first active agent is delivered to the middle to lower GI tract of a mammal to which the dual osmotic device is delivered: h) the first osmotic device provides a controlled delivery of the first active agent, and the second osmotic device provides a controlled delivery of the second active agent; i) the first and second active agents are delivered in one of a concurrent, sequential or overlapping manner; and/or j) the second semipermeable membrane loses its physical integrity within about 3–30 hours after administration.

The invention also provides a therapeutic device for the delivery of pharmaceutically active agents, ranging in solubility from slightly soluble to very soluble drugs, in a controlled, continuous and approximately steady, preferably zero order, rate over a prolonged period of time. Depending upon the excipients used, among other things, the osmotic device can also deliver drugs according to first order, or pseudo-first order release profiles. In addition, the osmotic device may provide targeted delivery of a drug.

The device of the present invention is optionally provided with an external coating disposed on the outside of the second osmotic device and comprising one or more active agents for immediate delivery to the environment of use.

Active agents useful in the delivery device include, for example, compounds such as biologically or pharmacologically active agents, medicines, nutrients, food products, insecticides, pesticides, herbicides, germicides, algaecides, fungicides, chemical reagents, growth regulating substances, parasiticides, sex sterilants, fertility promoters, biocides, rodenticides, disinfectants, anti-oxidants, plant growth promoters, preservatives, fermentation agents, fertility inhibitors, deodorants, micro-organism attenuators, catalysts, food supplements, cosmotics, vitamins, and other agents that benefit the environment of use.

Some specific embodiments of the invention include those wherein the active substance is pharmacologically or biologically active or wherein the environment of use is the GI tract of a mammal.

Other specific embodiments of the device of the invention are used in biological environments including the oral, ocular, nasal, vaginal, glandular, gastrointestinal tract, rectal, cervical, intrauterine, arterial, venous, otic, ophthalmic, sublingual, dermal, epidermal, subdermal, implant, buccal, bioadhesive, mucosal and other similar environments. Likewise, it may be used in aquariums, industrial warehouses, laboratory facilities, hospitals, chemical reactions and other facilities.

Other features, advantages and embodiments of the invention will become apparent to those of ordinary skill in the art by the following description, accompanying examples and appended claims.

BRIEF DESCRIPTION OF THE DRAWINGS

The following drawings are given by way of illustration only, and thus are not intended to limit the scope of the present invention. The drawings are not drawn to scale.

DETAILED DESCRIPTION OF THE INVENTION

The artisan of ordinary skill in the art of osmotic devices will understand the definitions of the terms "semipermeable membrane" and "porous membrane". By semipermeable membrane is meant a membrane that permits the influx of a liquid from the exterior of the delivery device to the interior of the delivery device, while at the same allowing release of the active agent in the core by osmotic pumping through the preformed passageway in the semipermeable membrane. By porous, or microporous, membrane is meant a membrane that permits release of the active agent in the core by diffusion through micropores or pores in a surrounding membrane.

Figure 1:
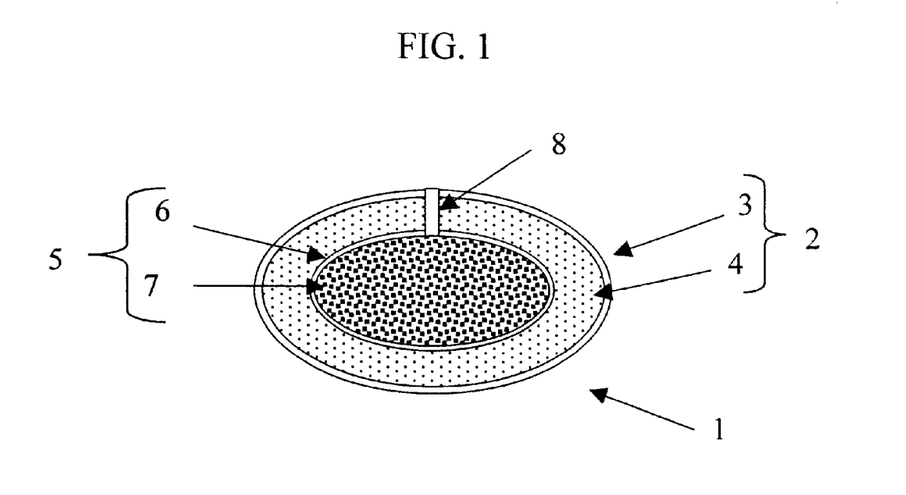
FIG. 1 depicts a sectional side view of a delivery device according to the present invention.

FIG. 1 depicts a dual osmotic delivery device (1) comprising a first osmotic device (5) and a second osmotic device (2). The first osmotic device (5) comprises a first semipermeable membrane (6) surrounding a first active agent-containing core (7). The second osmotic device (2) comprises a first semipermeable membrane (3) surrounding a second active agent-containing composition (4), which surrounds the first osmotic device (5). The dual osmotic device (1) has a passageway extending from the core (7) to the exterior of the device. A device made according to this embodiment will deliver the first and second active agents simultaneously for a period of time; although, the active agent may be released at the same or different rates. The active agent in the composition (4) can be released at a rate that is faster or slower than the rate of release of active agent from the core. Generally, most or all of the active agent in the composition (4) will be released before all of the drug in the core is released.

The delivery device (1) can be made by a process comprising the steps of: a) forming a compressed core comprising a first active agent; b) coating the compressed core with a first semipermeable membrane; c) surrounding the first semipermeable membrane with an active agent-containing composition comprising a second active agent; d) surrounding the active agent-containing composition with a second semipermeable membrane; and e) drilling an aperture through both the second and first semipermeable membranes and the active agent-containing composition. The artisan of ordinary skill will understand that the active agent-containing composition comprising the second drug can be applied as a sprayed-on or compression coat.

During use, the delivery device (1) is exposed to an aqueous environment of use comprising a fluid that can pass through the semipermeable membrane (3) and into the coating (4) thereby increasing the osmotic pressure of the second osmotic device to force delivery of the second active agent through the passageway (8). After a first period of time, i.e., during the middle stages of use, a sufficient amount of fluid has passed through the second osmotic device and entered into the first osmotic device to effect an osmotic pressure increase in the core of the first osmotic and force delivery of the first active agent through the passageway (8).

Figures 2, 3:
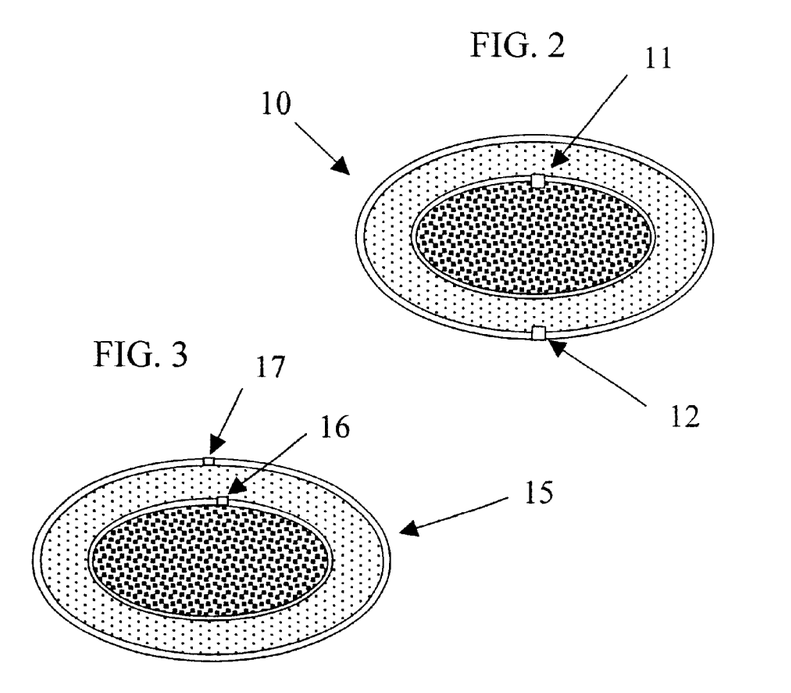
FIG. 2 depicts a sectional side view of an alternate delivery device according to the present invention.
FIG. 3 depicts a sectional side view of a second alternate delivery device.

The preformed passageways in the first and second semipermeable membranes need not be located adjacent each other. FIG. 2 depicts an alternate embodiment of a dual osmotic device made according to the invention. The dual osmotic device (10) comprises two distal, or opposing, passageways, wherein the first passageway (11) extends through the first (internal) semipermeable membrane, and the second passageway (12) extends through the second (external) semipermeable membrane. A dual osmotic device made according to this embodiment will generally deliver a majority of its second active agent from the coating before beginning delivery of its first active agent from the core.

The delivery device (10) can be made by a process comprising the steps of: a) forming a compressed core comprising a first drug; b) coating the compressed core with a first semipermeable membrane; c) forming at least one first passageway in the first semipermeable membrane; d) surrounding the first semipermeable membrane with a drug-containing composition comprising a second drug; e) surrounding the drug-containing composition with a second semipermeable membrane; and f) forming at least one passageway (aperture) through the second semipermeable membrane. The artisan of ordinary skill will understand that the drug-containing composition comprising the second drug can be applied as a sprayed-on or compression coat. Since the drug-containing composition comprising a second drug is applied after the first passageway(s) is(are) formed in the first semi-permeable membrane, the drug-containing composition comprising a second drug will plug the passageway(s). Therefore, when the dual osmotic device is placed in an aqueous environment of use, first drug will not be released from the core until the drug-containing composition comprising a second drug has been removed (by dissolution or erosion, for example) from the passageway(s).

The passageways in the first and second semipermeable membranes can be adjacent one another, but they need not communicate with one another as depicted in FIG. 1. FIG. 3 depicts another alternate embodiment of the dual delivery device. The device (15) comprises a first passageway (16) in the first semipermeable membrane and an adjacent but non-communicating second passageway (17) in the second semipermeable membrane. This device is made according to a process very similar to that used to make the device of FIG. 2 except that the passageways are located on the same face (half) of the dual osmotic device (15).

Each of the semipermeable membranes of the dual osmotic device can have one or more passageways. In addition, the dual osmotic device can be designed to provide a loading dose of a drug. The dual osmotic device (20) depicted in FIG. 4 comprises a compressed core (25) comprising a first drug composition comprising first drug, at least one pharmaceutical excipient, and at least one osmagent; a first semipermeable membrane (24) surrounding the core; plural first passageways (27) in the first semipermeable membrane; a second drug composition (23) surrounding the first semipermeable membrane, plugging the first passageways and comprising a second drug, at least one pharmaceutical excipient and at least one osmagent; a second semipermeable membrane (22) surrounding the second drug composition (23); at least one second passageway (26) in the second semipermeable membrane; and a rapid (immediate) release third drug composition surrounding the second semipermeable membrane, plugging the second passageway and comprising a third drug and at least one pharmaceutical excipient. The first, second and third drugs can be independently the same or different. The osmagent can be independently the same or different at each occurrence. The excipient can be independently the same or different at each occurrence. It should be noted that the second passageway (26) is larger than any of the first passageways depicted. Likewise, the first passageway can be larger than the second passageways. Alternately, there may be plural second passageways and a single first passageway.

Figure 4:
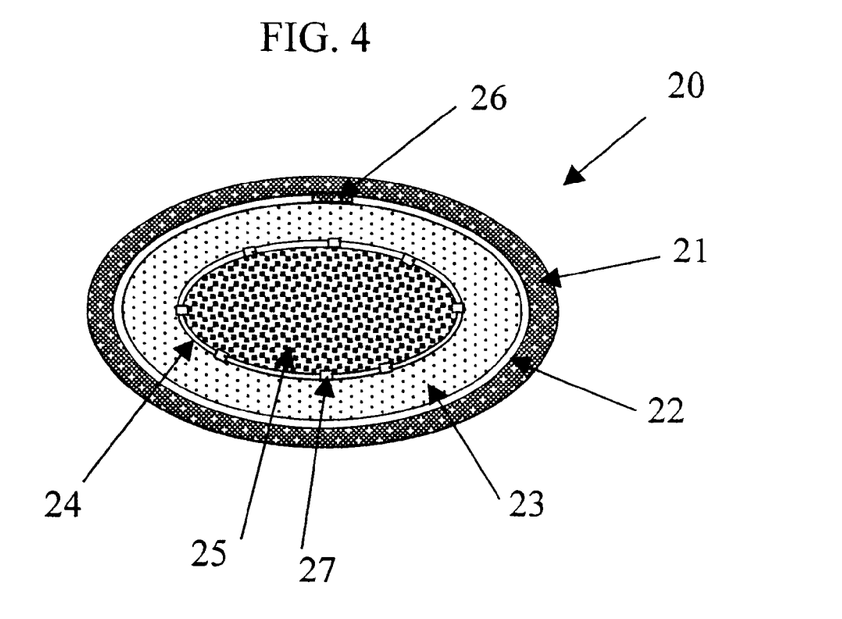
FIG. 4 depicts a sectional side view of a third alternate delivery device.

The dual osmotic device of FIG. 4 can be made according to a process comprising the steps of: a) forming a compressed core comprising a first drug composition comprising a first drug, at least one pharmaceutical excipient and at least one osmagent; b) coating the compressed core with a first semipermeable membrane; c) forming at least one first passageway in the first semipermeable membrane; d) surrounding the first semipermeable membrane with a second drug composition comprising a second drug, at least one pharmaceutical excipient and at least one osmagent; e) surrounding the second drug composition with a second semipermeable membrane; f) forming at least one passageway (aperture) through the second semipermeable membrane; and g) surrounding the second semipermeable membrane with a rapidly dissolving or eroding third drug composition comprising a third drug and at least one pharmaceutical excipient. The artisan of ordinary skill will understand that the second and third drug compositions can be applied as sprayed-on or compression coats. Since the second drug composition is applied after the first passageway(s) is(are) formed in the first semi-permeable membrane, the second drug composition will plug the first passageway(s). Likewise, the third drug composition will plug the passageways(s) in the second semipermeable membrane.

Controlled release rates of active agent provided by the individual osmotic devices will depend upon, among other things: a) the compositions of the osmotic devices; b) the solubility of the active agents; c) the disposition of the passageways in the semipermeable membranes; d) the presence or absence of additional membranes or coatings surrounding the second osmotic device; e) the presence or absence of additional membranes or coatings surrounding the semipermeable membrane of the first osmotic device; f) the diffusivity of the active agents through the semipermeable membranes; g) the presence or absence of additional membranes or coatings surrounding the first osmotic device; h) the presence or absence of an expandable hydrophilic osmopolymer in the core of the first osmotic device and/or in the coating of the second osmotic device; and i) the size and number of passageways in the semipermeable membranes.

In a preferred embodiment, the second, and optionally the first, semipermeable membrane becomes highly porous and/or loses its physical integrity towards the end of use. For example, it may be preferred to provide a second semipermeable membrane that loses its physical integrity after at least a majority of the second drug composition has been released. The semipermeable membranes are preferably physiologically inert.

The dual osmotic device of the invention can independently deliver the active agents in the osmotic devices according to zero, first order, pseudo-first order, second order, pseudo-second order, third order and pseudo-third order release profiles. The mechanisms of active agent delivery from the core can include delayed, pH dependent, pH independent, sustained, controlled, and/or targeted release. Accordingly, the release profiles of the active agents included in the osmotic devices are generally independent of one another. If a combined osmotic device also comprises an external coating containing a third drug, the release of the third drug will be independent of the release of the first and second drugs, and the release of the third drug will generally be rapid. In each occurrence, the first, second and third drugs are independently the same or different, meaning that all three of the drugs are the same or different or at least two of the drugs are the same.

When the active agent is poorly soluble in water and has a low diffusivity, the aqueous suspension of the active agent is mainly released to the environment of use through the at least one passageway of the semipermeable membrane in a controlled manner over a prolonged first period of time.

As used herein, the terms "very soluble", "freely soluble", "soluble", "sparingly soluble", "slightly soluble", "very slightly soluble", and "practically insoluble" or "insoluble" are defined as they are defined in the U.S.P. 23$^{rd}$ Ed. as follows:

| Term | Solubility of component in water (parts of solvent per part of component) |
| --- | --- |
| Very soluble | <1 |
| Freely soluble | 1–10 |
| Soluble | 10–30 |
| Sparingly soluble | 30–100 |
| Slightly soluble | 100–1,000 |
| Very slightly soluble | 1,000–10,000 |
| Practically insoluble of insoluble | Over 10,000 |

The formulation of the present delivery device can be changed to permit optimal delivery of slightly, sparingly and very soluble active agents to an aqueous environment of use.

The delivery device of the invention can include one or more water soluble coats. Those coats are independently selected at each occurrence from an inert coat, an enteric coat, a drug release-controlling coat, and a microporous coat.

If a microporous membrane is incorporated into the dual osmotic device, the micropores in the wall are not formed by mechanical means. The micropores are formed during preparation of the wall or during exposure to fluids in an intended environment of use. Methods of preparing walls wherein the micropores form in the environment of use are well known and described in, among others, U.S. Pat. Nos. 3,845,770, 3,916,899, 4,063,064, 4,088,864, 4,816,263, 4,200,098, 4,285,987 and 5,912,268, the relevant disclosures of which are hereby incorporated by reference. Generally, a microporous membrane is formed by including soluble materials (powdered, crystalline or particulate) into the composition used to form the membrane on the surface of a solid substrate such that when the formed membrane is exposed to an appropriate fluid in an environment of use, the soluble material dissolves leaving behind pores in the formed membrane rendering it porous or microporous.

When the delivery device includes a water soluble coat between the first and second osmotic devices, the water soluble coat will cause a delay in the release of the active agent from the interior first osmotic as compared to release of active agent from the exterior second osmotic device.

A release-controlling coat will control either the rate or relative time of release of an active agent enclosed within the release-controlling coat. For example, if a release controlling coat surrounds the semipermeable membrane of the interior osmotic device, the release-controlling coat will control the release of active agent from that osmotic device.

The additional coats described herein can be located between the core and semipermeable membrane of the interior osmotic device, between the first and second osmotic devices, between the active agent composition and the semipermeable membrane of the exterior osmotic device or exterior to the semipermeable membrane of the exterior osmotic device.

Swellable hydrophilic polymers suitable for the dual osmotic device include hydrophilic polymers that interact with water and/or aqueous biological fluids, and swell and retain water within their structure. The core, and/or active agent-containing coating preferably expand to about 2 to 50 times of their initial volume. The polymers are preferably slightly cross-linked. Uncross-linked polymers will preferably not dissolve in water, keeping their physical integrity. The polymers are of animal, plant or synthetic origin. Hydrophilic polymers suitable for manufacturing the core of the invention preferably include hydroxypropyl methylcelluloses (viscosity from 3 to 100,000 cps, measured in 2% w/v solution); ethylcelluloses (viscosity from 3 to 110 cP, measured in 5% w/v solution); methylcelluloses (viscosity from 10 to 10,000 cP, measured in 2% w/v solution); hydroxypropylcelluloses (general average molecular weight of about 80,000 to 1,150,000); hydroxyethylcelluloses (viscosity from 2 to 21,000 cP, measured in 2% w/v solution); carboxymethylcelluloses (viscosity from 5 to 4,000 cP, measured in 1% w/v solution); poly (alkylene) oxide that might include homopolymer of ethylene oxide, propylene oxide and butylene oxide and copolymers of those.

The poly(alkylene oxides) used herein preferably have an average molecular weight of about 1,000,000 to 2,000,000 (viscosity around 400–800 and 2,000–4,000 cP, measured in 2% w/v solution), or an average molecular weight around 4,000,000 to 8,000,000 (viscosity around 1,650–5,500 and 10,000–15,000 cP, measured in 1% w/v solution).

The composition of the semipermeable membrane is varied as desired to prepare osmotic devices having particular release profiles of active agent. Generally, a cellulose esters (CE) and/or a copolymer of methacrylate salts (CM) and optionally a plasticizer (P) are used.

Representative cellulose esters useful in the membrane of the invention include cellulose acylate; mono, di and tricellulose alkanylates; mono, di and tricellulose aroylates; cellulose propionate; cellulose acetate-butyrate; cellulose triacylates such as cellulose trivalerate, cellulose trilaurate, cellulose tripalmitate, cellulose trisuccinate; cellulose diacylates such as cellulose disuccinate, cellulose dipalmitate; combinations thereof and other cellulose esters used by those of ordinary skill in the art in the preparation of controlled delivery devices and membranes.

The poly(methacrylate) copolymer salts used in the manufacturing of the membrane preferably include: poly (ammonium methacrylate) copolymer RL (Eudragit™ RL), poly(ammonium methacrylate) copolymer (type A-USP/ NF), poly(aminoalkyl methacrylate) copolymer RL-JSP I), and (ethyl acrylate)-(methyl methacrylate)- [(trimethylammonium)-ethylmethacrylate] (1:2:0.2) copolymer, MW 150,000. More preferred polymers include (Röhm Pharma, Weiterstadt): Eudragit™ RS 100: solid polymer, Eudragit™ RL 12.5: 12.5% solution in solvent, Eudragit™ RL 30 D: 30% aqueous dispersion, and other equivalent products.

The following poly (ammonium methacrylate) copolymers can also be used: ammonium methacrylate copolymer RS (Eudragit™ RS), poly(ammonium methacrylate) copolymer (type B-USP/NF), poly(aminoalkyl methacrylate) copolymer (RSL-JSP I), (ethyl acrylate)-(methyl methacrylate)-[(trimethylammonium)-ethyl methacrylate] (1:2:0.1) copolymer, PM 150,000. More preferred polymers include (Röhm Pharma, Weiterstadt): Eudragit™ RS 100: solid polymer, Eudragit™ RS 12.5: 12.5% solution in solvent, Eudragit™ RS 30 D: 30% aqueous dispersion and other equivalent products. Eudragit™ RL is readily water permeable while Eudragit™ RS is hardly water permeable. By employing mixtures of both Eudragit™ RL and Eudragit™ RS, membranes having the desired degree of permeability are prepared.

Plasticizers that can be used in the membrane of the invention include all those that are generally incorporated into polymeric coatings of delivery devices. Plasticizers generally improve the mechanical properties and increase the flexibility of the polymeric film. Plasticizers generally reduce cohesive intermolecular forces and increase mobility of polymer chains, thus reducing polymer-polymer interactions. This action is responsible for the changes to the properties of the polymers and films thereof such as a reduction of Tg (glass transition temperature) or softening temperature and the elastic module, increasing polymer flexibility, thus facilitating the process of formation of the membrane or film. A preferred pharmaceutical plasticizer is non-toxic and non-irritating; has a reduced tendency to migrate, extrude or volatilize; and has good miscibility with the polymers in film. Plasticizers that are used in the wall of the present invention include, for example, acetyl triethyl citrate, acetyl tributyl citrate, triethyl citrate, acetylated monoglycerids, glycerol, polyethylene glycol, triacetin, propylene glycol, dibutyl phthalate, diethyl phthalate, isopropyl phthalate, dimethyl phthalate, dactyl phthalate, dibutyl sebacate, dimethyl sebacate, castor oil, glycerol monostearate, fractionated coconut oil, and others. Preferably, polyethylene glycol is used, for example PEG 400, which is available from suppliers such as Aldrich, Sigma Chemical Co. and others.

Suitable plasticizers also include, by way of example and without limitation, low molecular weight polymers, oligomers, copolymers, oils, small organic molecules, low molecular weight polyols having aliphatic hydroxyls, ester-type plasticizers, glycol esters, poly(propylene glycol), multi-block polymers, single-block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. A combination of plasticizers may also be used in the present formulation. The PEG based plasticizers are commercially available or can be made by a variety of methods, such as disclosed in Poly (*ethylene glycol*) *Chemistry: Biotechnical and Biomedical Applications* (J. M. Harris, Ed.; Plenum Press, NY) the disclosure of which is hereby incorporated by reference.

Exemplary passageways include an orifice, hole, bore, aperture or the like, through which the active agent is released. Mechanical perforation, such as drill or laser perforation, punching a hole through the semipermeable membrane, employing a tablet punch having a pin to punch a hole through the semipermeable lamina, or any other method known to the artisan of ordinary skill in the art is used to form the passageways. Although each one of the osmotic devices in the dual osmotic device is depicted with a single passageway, each osmotic device according to the present invention can independently comprise one or more passageways including two, three, four, five, six, seven, eight, nine, ten or more passageways. The one or more passageway/s are formed in any place of the osmotic devices or as provided herein. The maximum and minimum dimensions of the passageway are preferably as disclosed in U.S. Pat. No. 3,845,770 (AR 199,301). As described herein, a passageway is a preformed passageway, meaning one that is formed by mechanical or other such means. During manufacture of a dual osmotic device according to the invention, a passageway may be plugged with a soluble or erodible composition (with or without active agent) after formation of the passageway. However, when the dual osmotic device is placed in an environment of use, the soluble composition will dissolve or erode to reveal the preformed passageway. A preformed passageway is considered different than a micropore or other such aperture formed as described above by inclusion of a pore-forming soluble material in sufficient quantities in the composition used to make a semipermeable membrane such that the pore-forming material dissolves in an environment of use leaving behind the microporous or porous membrane.

The dual osmotic device of the present invention can, optionally, include an external coating comprising an active agent for immediate delivery to the environment of use. Useful materials for the external coating include poly (vinylpyrrolidone) (PVP), poly(ethylene glycol) (PEG), hydroxypropyl ethylcellulose, hydroxypropyl methylcellulose, ethylcellulose, hydroxyethylcellulose, sodium carboxymethyl cellulose, dimethylaminoethyl methacrylate-methacrylate acid ester copolymer, soluble polysaccharide gums such as carrageenan, tragacanth, pectin, guar, combinations thereof and other such materials known by those of ordinary skill in the art. The external layer is dissolved, eroded or completely removed in the environment of use and provides an immediate delivery of the active agent to the environment of use. The active agent comprises about 0.1 to 99.9% by weight of the external coating.

The quantity of active agent present in the individual osmotic devices may independently vary between 0.10 and 99.9% by weight of each of their individual weights.

Osmotically effective compounds, such as osmotic agents or osmagents, that are capable of being totally or partially solubilized in the fluid may be added. Osmagents or osmotically effective compounds are generally soluble in the fluid that enters into the device through the semipermeable membranes creating an osmotic pressure gradient across the wall. The fluid, active agents and other components will generally form a solution or suspension comprising the active agent to be delivered. Exemplary osmagents include high or low molecular weight compounds, organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials known to those of ordinary skill in the art. Preferred osmagents include potassium chloride, sodium tartrate, glucose, mannitol, sodium acetate, sodium chloride, sodium sulfate, sodium citrate, potassium tartrate, sorbitol, sucrose and combinations thereof. An osmopolymer can also be used in the device as an osmotically effective agent.

The delivery device of the invention advantageously requires lower amounts of osmagent, osmopolymer or osmotically effective agent to deliver an active substance than is required by related osmotic devices containing the same amount of active substance. Accordingly, the present delivery device contains a higher relative loading of active substance than other comparable osmotic devices containing the same absolute amount of active substance, and is generally smaller and lighter than such other devices. In preferred embodiments, the percentage of active substance present in the entire device ranges from about 0.1% to about 99% with respect to the total weight of the device.

The tablets of the invention can also comprise an acidifying agent, alkalizing agent, adsorbent, antioxidant, buffering agent, colorant, flavorant, sweetening agent, tablet antiadherent, tablet binder, tablet and capsule diluent, tablet direct compression excipient, tablet disintegrant, tablet glidant, tablet lubricant, tablet or capsule opaquant and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other such materials known to those of ordinary skill in the art.

As used herein, the term "antioxidant" is intended to mean an agent who inhibits oxidation and is thus used to prevent the deterioration of preparations by the oxidative process. Such compounds include, by way of example and without limitation, ascorbic acid, ascorbic palmitate, Vitamin E, butylated hydroxyanisole, butylated hydroxytoluene, hypophosphorous acid, monothioglycerol, propyl gallate, sodium ascorbate, sodium bisulfite, sodium formaldehyde sulfoxylate, sodium metalbisulfite and other such materials known to those of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium for product stability. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art.

As used herein, the term "buffering agent" is intended to mean a compound used to resist a change in pH upon dilution or addition of acid or alkali. Such compounds include, by way of example and without limitation, potassium metaphosphate, potassium phosphate, monobasic sodium acetate and sodium citrate anhydrous and dehydrate and other such materials known to those of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol, sucrose, fructose and other such materials known to those of ordinary skill in the art.

As used herein, the expression "antiadherent" is intended to mean an agent that prevent the sticking of tablet formulation ingredients to the punches and dies in a tableting machine during production. Such compounds include, by way of example and without limitation, magnesium stearate, calcium stearate, talc, glyceryl behenate, poly(ethylene glycol), hydrogenated vegetable oil, mineral oil, stearic acid, combinations thereof and other such materials known to those of ordinary skill in the art.

As used herein, the term "binder" is intended to mean a substance used to cause adhesion of powder particles in tablet granulations. Such compounds include, by way of example and without limitation, acacia, alginic acid, tragacanth, carboxymethylcellulose sodium, poly(vinylpyrrolidone), compressible sugar (e.g., NuTab), ethylcellulose, gelatin, liquid glucose, methylcellulose, povidone and pregelatinized starch, combinations thereof and other materials known to those of ordinary skill in the art.

When needed, other binders may also be included in the present osmotic device. Exemplary binders include starch, poly(ethylene glycol), guar gum, polysaccharide, bentonites, sugars, invert sugars, poloxamers (PLURONIC™ F68, PLURONIC™ F127), collagen, albumin, celluloses in non-aqueous solvents, combinations thereof and the like. Other binders include, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

As used herein, the term "tablet direct compression excipient" is intended to mean a compound used in direct compression tablet formulations. Such compounds include, by way of example and without limitation, dibasic calcium phosphate (e.g. Ditab™), microcrystalline cellulose, direct compression lactose (e.g. Tablettose™, Lactose DT), combinations thereof and other such materials known to those of ordinary skill in the art.

As used herein, the term "glidant" is intended to mean agents used in tablet and capsule formulations to improve flow-properties during tablet compression and to produce an anti caking effect. Such compounds include, by way of example and without limitation, colloidal silica, calcium silicate, magnesium silicate, silicon hydrogel, cornstarch, talc, combinations thereof and other such materials known to those of ordinary skill in the art.

As used herein, the term "lubricant" is intended to mean substances used in tablet formulations to reduce friction during tablet compression. Such compounds include, by way of example and without limitation, calcium stearate, magnesium stearate, mineral oil, stearic acid, zinc stearate, combinations thereof and other such materials known to those of ordinary skill in the art.

As used herein, the term "tablet opaquant" is intended to mean a compound used to used in tablet coatings or capsules providing useful opacity which can aid the stability to the light in case of sensitive agents. It may be used alone or in combination with a colorant. Such compounds include, by way of example and without limitation, titanium dioxide and other such materials known to those of ordinary skill in the art.

As used herein, the term "tablet polishing agent" is intended to mean a compound used to impart brightness to the surface of the coated tablets. Such compounds include, by way of example and without limitation, carnauba wax, white wax, combinations thereof and other such materials known to those of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g. Avicel™), carboxymethylcellulose calcium, cellulose polyacrylin potassium (e.g. Amberlite™), alginates, sodium starch glycolate, gums such as agar, guar, locust bean, karaya, pectin, tragacanth, combinations thereof and other such materials known to those of ordinary skill in the art.

As used herein, the term "colorant" is intended to mean a compound used to impart color to pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and iron oxide (black, red, yellow), other F.D. & C. dyes and natural coloring agents such as grape skin extract, beet red powder, beta-carotene, annato, carmine, turmeric, paprika, combinations thereof and other such materials known to those of ordinary skill in the art.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors, which have been found to be particularly useful, include commercially available orange, grape, cherry and bubble gum flavors and mixtures thereof. The amount of flavoring may depend on a number of factors, including the desired organoleptic effect. Flavors will be present in any amount as desired by the artisan of ordinary skill in the art. Particularly preferred flavors are the grape and cherry flavors and citrus flavors such as orange.

The delivery device of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides and acetylated fatty acid glycerides. The device can also include alcohol such as ethanol, isopropanol, hexadecyl alcohol, glycerol and propylene glycol; glycerol ketals such as 2,2-dimethyl-1, 3-dioxolane-4-methanol; ethers such as poly(ethyleneglycol) 450; petroleum hydrocarbons such as mineral oil and petrolatum; water; mixtures thereof; or a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents such as dimethyl dialkyl ammonium halides, alkyl pyridinium halides, and alkylamine acetates; anionic detergents such as alkyl, aryl and olefin sulfonates, alkyl, olefin, ether and monoglyceride sulfates, and sulfosuccinates; non-ionic detergents such as fatty amine oxides, fatty acid alkanolamides, and poly(oxyethylene)-block-poly(oxypropylene) copolymers; amphoteric detergents such as alkyl β-aminopropionates and 2-alkylimidazoline quaternary ammonium salts; and mixtures thereof.

Various other components, not otherwise listed above, can be added to the present formulation to provide a device with a desired release profile. Such components include, by way of example and without limitation, glycerylmonostearate, nylon, cellulose acetate butyrate, d,l-poly (lactic acid), 1,6-hexanediamine, diethylenetriamine, starches, derivatized starches, acetylated monoglycerides, gelatin coacervates, poly(styrene-maleic acid) copolymer, glycowax, castor wax, stearyl alcohol, glycerol palmitostearate, poly ethylene, poly(vinyl acetate), poly (vinyl chloride), 1,3-butylene-glycoldimethacrylate, ethyleneglycol-dimethacrylate and methacrylate hydrogels.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

Active agents generally include physiologically or pharmacologically active substances that produce a systemic or localized effect or effects on animals and human beings. Active agents also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleaning, confectionery and flavoring applications. The active agent can be present in its neutral, ionic, salt, basic, acidic, natural, synthetic, diastereometric, isomeric, enantiomerically pure, racemic, hydrate, chelate, derivative, analog, or other common form.

When the active agent is a therapeutic compound, exemplary therapeutic compounds include antibiotics, antihistamines and decongestants, antiinflammatory agents, antiparasitics, antivirals, local anesthetics, antifungal agents, amoebicidal agents, trichomonocidal agents, analgesics, antiarthrits agents, anthiasthmatics, anticoagulants, anticonvulsants, antidepressants, antidiabetics, antineoplastics, antipsychotics, neuroleptics, antihypertensives, antidepressants, hypnotics, sedatives, anxyolitic energizers, anti-convulsants, antiparkinson agents, muscle relaxant agents, antimalarials, hormonal agents, contraceptives, sympathomimetics, diuretics, hypoglycemics, ophthalmics, electrolytes, diagnostic agents and cardiovascular drugs.

Representative antibacterial substances include, for example, penicillins: penicillin G and V, penicillinase-resistant penicillin (methicillin, nafcillin, oxacilin, cloxacilin and dicloxacillin), and aminopenicillins: ampicillin, amoxicillin, cyclacillin; carboxy and ureidopenicillines such as carbenicillin, ticarcillin, azlocillin, mezlocillin and piperacilllin; cephalosporins such as the first-generation cephalosporins such as cephalotin, cephalexin, cefazolin, second generation cephalosporins such as cefoxitin, cefaclor, cefuroxime, and third generation cephalosporins such as cefotaxime, ceftriaxone,ceftazidime; beta-lactam antibiotics such as imipenem, aztreonam; sulfonamides such as sulfisoxazole, sulfamethoxazole, sulfadiazine, sulfasalazine and trimethropim-sulfamethoxazole; tetracyclines such as oxytetracycline, methacycline, chlorotetracycline and doxycycline; chloramphenicol, erythromycin, lincomycin, clindamycin, vancomycin, bacitracin; aminoglycoside antiobiotics such as streptomycin, gentamicin, tobramycin, amikacin, kanamycin and neomycin; and quinolones such as nalidixic acid, norfloxacin, ciprofloxacin, cinoxacin, ofloxacin, enoxacin, lomefloxacin, amifloxacin and pefloxacin.

Representative antiparasitic compounds include anthelmintics such as ivermectin, mebendazole, albendazole, piperazine, praziquantel, thiabendazole, and dapsone. Representative anti-malarial compounds include chloroquine and its congeners, diaminopyrimidines, mefloquine, primaquine and pyrimethamine. Miscellaneous antiparasitic agents include 8-hydroxyquinolines, metronidazole, quinacrine and paromomycin.

Representative antiviral compounds include acyclovir, gancyclovir, pencyclovir, foscarnet, idoxuridine, trifluridine and vidarabine; anti-retroviral compounds such as zidovudine, didadosine, estavudine; and others such as interferon, amantadine and rivavirine.

Representative antineoplastics include nitrogen mustards such as mechlorethamine chlorambucil, cyclophosphamide; ethylenimines and methylmelamines such as triethylenemelamine, thiotepa, hexamethyl-melamine; alkyl sulfonates such as busulfan; nitrosureas such as carmustine (BCNU), lomustine; dacarbazine; folic acid analogs such as methotrexate; pyrimidine analogs such as fluorouracil, arabinoside cytisine; purine analogs such as mercaptopurine, azathiprine; vinca alkaloids such as vincristine, vinblastine, taxol; etoposide; antibiotics such as actinomycin D, daunorubicin, doxorubicin, bleomycin, mitomycin; cisplatin; hydroxyurea; procarbazine; aminoglutethimide; cisplatin and tamoxifen.

Representative anti-inflammatory and analgesic drugs include cortisone, hydrocortisone, prednisone, prednisolone, betamethasone, dexamethasone and fluorocortisone; salycilates such as salycilic acid, aspirin and diflunisal; pyrazolon derivates such as phenylbutazone and oxyphenbutazone; aminopyridines such as dipyrone, paraaminophenol derivates such as acetaminophen and phenacetin, indomethacin and sulindac; fenamates such as mefenamic acid; tolmetin; propionic acid derivates such as ibuprofen, naproxen, fenoprofen, ketoprofen, flurbiprofen and indoprofen; piroxicam, and diclofenac. Representative opoid analgesics include morphine, codeine, meperidine and nalorphine.

Representative drugs used in the treatment of gout include colchicine, allopurinol, probenecid and sulphinpirazone.

Representative antihistamines and decongestants include the first generation compounds such as diphenhydramine, pirilamine, chlorpheniramine, brompheniramine, promethazine; and second-generation compounds such as astemizole, loratadine and terfenadine.

Representative sympathomimetic drugs include epinephrine, amphetamine, ephedrine and norepinephrine.

Representative antiasthmatic drugs include methylxanthines such as theophylline; from corticoids such as beclomethasone dipropionate, budesonide, flunisolide, prednisone; bronchodilators such as albuterol, salbutamol, salmetherol, terbutaline; antimuscharinic agents such as ipratopium bromide; and cromolyn sodium.

Representative local anesthetics include benzocaine, procaine, lidocaine, cocaine, tetracaine, bupivacaine and dibucaine.

Representative muscle relaxants and antispasmodic agents include baclofen, succinylcholine, dantrolene, carisoprodol, metaxalone, cyclobenzaprine, diazepan, mephensin, trihexylphenidyl and biperiden. Representative antiparkinson disease compounds include levodopa, carbidopa, benceracide, amantadine, bromocriptine and pergolide.

Representative antidepressant include tricyclic agents such as amitriptyline, imipramine, clomipramine, doxepine; monoamine oxidase inhibitors such as isocoboxazid, phenelzine and tranylcypromine; fluoxetine, fluvoxamine, paroxetine, sertraline, venlafaxine, bupropione and trazodone.

Representative anticonvulsants include hydantoins such as phenytoin, barbiturates and deoxy derivates such as phenobarbital and primidone; carbamazepine, ethosuximide, valproic acid; and benzodiacepines such as diazepam and clonazepam.

Representative antipsychotics include chlorpromazine, trifluoperazine, thioridazine, fluphenazine, perphenazine, haloperidol, loxapine, molindone, clozapine, pimozide, risperidone and lithium.

Representative hypnotics and sedatives include barbiturates such as pentobarbital sodium, phenobarbital, secobarbital, thiopental; benzodiazepines such as diazepam, alprazolam, chlordiazepoxide, clonazepam, lorazepam, oxazepam; buspirone, meprobamate, zolpidem and zoplicone.

Representative hypoglycemic agents include insulin, insulin zinc, isophane insulin, protamine zinc insuline and extended insulin zinc suspension; sulfonylureas such as tolbutamide, chlorpropamide, acetohexamide, glyburide, glipizide, glicazide; biguanides such as phenformin, metformin; ciglitazone, troglitazone, and acarbose.

Representative antidiuretics drugs include inhibitors of carbonic anhydrase such as acetazolamide, chortalidone, indapamine; benzothiadiazides such as chlorothiazide, hydrochlorothiazide; ethacrynic acid, furosemide, bumetanide; aldosterone antagonists such as spironolactone; triamtirene and amiloride.

Representative antihypertensive and cardiovascular drugs include inhibitors of the renin-angiotensin system such as enalapril, lisinopril, ramipril, captopril, perindopril, trandolapril; angiotensin II receptors antagonists such as losartan; calcium channel blockers: nifedipine, amlodipine, nitrendipine, nimodipine, diltiazem, verapamil; simpathocolitic agents; adrenergic antagonists: atenolol, propanolol, nadolol, sotalol, timolol, metropolol, acebutolol, carvedilol; adrenergic agonists; prazosin, fentolamine; centrally acting agents such as methyldopa, clonidine, guanfacine, reserpine; direct arterial and venous vasodilators such as sodium nitroprusside, nitroglicerin, isosorbide 5-mononitrate, isosorbide dinitrate; antiarrithmic agents such as quinidine, procainamide, phenytoin, lidocaine, mexiletine, propafenone, flecainide, encainide, propranolol, acebutolol, amiodarone, sotalol, verapamil and diltiazem; digitalis; and cardiac glycosides such as digoxine, digitoxine, amrinone, and milrinone.

Representative anticoagulants include heparin, dicoumarol; thrombolytic agents such as streptokinase, tissue plasminogen activator (t-PA) urokinase and antiplatelet drugs such as dipyridamole, ticlopidine, and sulfinpyrazone.

Representative prokynetic gastrointestinal drugs include cisapride, domperidone, and metoclopramide.

Representative anti-spasmodic and muscle contractants include atropine, scopolamine, methoescopolamine and oxyphenonium.

Representative steroidal drugs include prednisolone, cortisone, cortisol and triamcinolone; androgenic steroids such as methyltesterone, and fluoxmesterone; estrogenic steroids such as 17β-estradiol, α-estradiol, estriol, α-estradiol 3 benzoate, and 17-ethynylestradiol-3-methyl ether; and progestational steroids such as progesterone, 19-nor-pregn-4-ene-3,20-dione, 17-hydroxy-19-nor-17-α-pregn-5(10)-ene-20-yn-3-one, 17α-ethynyl-17-hydroxy-5 (10)-estren-3-one, and 9β, 10α-pregna-4,6-diene-3,20-dione.

Representative ophthalmic agents include pilocarpine, pilocarpine salts such as pilocarpine nitrate, pilocarpine hydrochloride, dichlophenamide, atropine, atropine sulfate, scopolamine and eserine salicylate.

Representative nutritional agents include ascorbic acid, niacin, nicotinamide, folic acid, choline biotin, panthothenic acid, and vitamin B12, essential amino acids, and essential fats.

Representative electrolytes include calcium gluconate, calcium lactate, potassium chloride, potassium sulfate, sodium chloride, sodium fluoride, ferrous lactate, ferrous gluconate, ferrous sulfate, ferrous fumarate and sodium lactate.

The above-mentioned list should not be considered exhaustive and is merely exemplary of the many embodiments considered within the scope of the invention. Many other active compounds can be administered with the device of the present invention.

The therapeutic compound(s) contained within the present device can be formulated as its pharmaceutically acceptable salts. As used herein, "pharmaceutically acceptable salts" refers to derivatives of the disclosed compounds wherein the therapeutic compound is modified by reacting it with an acid or base as needed to form an ionically bound pair. Examples of pharmaceutically acceptable salts include conventional non-toxic salts or the quaternary ammonium salts of the parent compound formed, for example, from non-toxic inorganic or organic acids. Suitable non-toxic salts for basic active agents include those derived from inorganic acids such as hydrochloric, hydrobromic, sulfuric, sulfonic, sulfamic, phosphoric, nitric and others known to those of ordinary skill in the art. The salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and others known to those of ordinary skill in the art. Suitable non-toxic salts for acidic active agents include those derived from an organic amine, an alkali metal hydroxide, an alkali metal alkoxide, a primary amine, a secondary amine, a tertiary amine, a quaternary amine, an aromatic amine, a heterocyclic amine, or an inorganic base. The pharmaceutically acceptable salts of the present invention can be synthesized from the parent therapeutic compound which contains a basic or acidic moiety by conventional chemical methods. Lists of other suitable salts are found in *Remington's Pharmaceutical Sciences*, 17$^{th}$. ed., Mack Publishing Company, Easton, Pa., 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

As used in this disclosure, the term vitamin refers to trace organic substances that are required in the diet. For the purposes of the present invention, the term vitamin(s) include, without limitation, thiamin, riboflavin, nicotinic acid, pantothenic acid, pyridoxine, biotin, folic acid, vitamin B12, lipoic acid, ascorbic acid, vitamin A, vitamin D, vitamin E and vitamin K. Also included within the term vitamin are the coenzymes thereof. Coenzymes are specific chemical forms of vitamins and can include thiamin pyrophosphates (TPP), flavin mononucleotide (FMN), and flavin adenine dinucleotive (FAD). Nicotinamide adenine dinucleotide (AND), Nicotinamide adenine dinucleotide phosphate (NADP), Coenzyme A (CoA), pyridoxal phosphate, biocytin, tetrahydrofolic acid, coenzyme B12, lipolysine, 11-cis-retinal, and 1,25-dihydroxycholecalciferol. The term vitamin(s) also includes choline, camitine, and alpha, beta, and gamma carotene.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium, mixtures thereof and others known to those of ordinary skill in the art.

The term "dietary supplement" as used herein means a substance, which has an appreciable nutritional effect when, administered in small amounts. Dietary supplements include, without limitation, such ingredients as bee pollen, bran, wheat germ, kelp, cod liver oil, ginseng, and fish oils, amino-acids, proteins, plant extracts, plant powder, herbs, herbal extracts and powders, vitamins, minerals, combinations thereof and others known to those of ordinary skill in the art. As will be appreciated, essentially any dietary supplement may be incorporated into the present osmotic device.

The amount of therapeutic compound incorporated in each device of the invention will be selected according to known principles of pharmacy. An effective amount of therapeutic compound is specifically contemplated. By the term "effective amount", it is understood that, with respect to, for example, pharmaceuticals, a pharmaceutically effective amount is contemplated. A pharmaceutically effective amount is the amount or quantity of a drug or pharmaceutically active substance which is enough for the required or desired therapeutic response, or in other words, the amount, which is sufficient to elicit an appreciable biological response when, administered to a patient. The appreciable biological response may occur as a result of administration of single or multiple unit doses of an active substance. Depending upon the active substance used and upon the amount of active substance present in a particular device according to the invention, a unit dose may comprise one or more such devices. As used with reference to a vitamin or mineral, the term "effective amount" means an amount at least about 10% of the United States Recommended Daily Allowance ("RDA") of that particular ingredient for a patient. For example, if an intended ingredient were vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

For oral, buccal, and sublingual administration, the delivery device may be in the form of a caplet or tablet. For rectal administration, the osmotic device can be included in a suppository or tablet for release of a therapeutic compound into the intestines, sigmoid flexure and/or rectum. For cutaneous, subcutaneous, otic, intraperitoneal, ophthalmic and implant applications, the device is a solid dosage form adapted for such application and is preferably a tablet. Bioavailability enhancers such as alcohols or other compounds that enhance the penetration of the therapeutic compound from the delivery device into the mucosa may be needed to prepare suitable formulations.

The device of the invention can be prepared according to the methods disclosed herein or those well known in the art. For example, according to a preferred process, the hydrophilic polymer or a mixture thereof is mixed with suitable excipients in solid form and an active agent and then compressed to form the core of the first osmotic device. The core is preferably 6 to 12 mm in diameter. The cores are then covered preferably with a mixture of selected polymers that constitute the first semipermeable membrane. Subsequently, the first semipermeable membrane is perforated at any location with a laser, drill or other mechanical means known to those of ordinary skill in the art. Optionally, the first semipermeable membrane is perforate at about the same time that the second semipermeable membrane is permeated. The first osmotic device is then compression or spray-coated with an active agent-containing coating, which is then coated with a composition used that forms the second semipermeable membrane. The second semipermeable membrane is then perforated with a laser, optionally while simultaneously perforating the first semipermeable membrane.

If desired, the device of the invention can be coated with a finish coating as is commonly done in the art to provide the desired shine, color, taste or other aesthetic characteristics. Materials suitable for preparing the finish coating are well known to those of ordinary skill in the art.

The following examples should not be considered exhaustive, but merely illustrative of only a few of the many embodiments contemplated by the present invention. The methods described herein can be followed to prepare osmotic devices according to the invention.

EXAMPLE 1

A large scale batch of montelukast (10 mg strength) and loratadine (10 mg strength) tablets is prepared by mixing 10.4 g of sodium montelukast, 70.6 g of mannitol, and 12.0 g of povidone to form a mixture. The mixture is wet with a blend of 36.00 ml of alcohol 96°, 2.3 g of PEG 400 and 10.0 g if PEG 6000 to form a blend. The blend is granulated and dried at 40–50° C. for 3 hours; then, it is screened and mixed with 2.0 g of colloidal silicon dioxide. The blend is mixed to homogeneity and 2.70 g of magnesium stearate is added as lubricant. The final blend is tabletted using biconcaves, 6.50-mm diameter punches. Core weight: 110.0 mg. Hardness from 6–10 P.

A first composition to cover the cores is prepared as follows: 24.7 g of cellulose acetate and 1.3 g of polyethylene glycol 400 in a mixture of 710 ml of acetone and 290 ml of methyl alcohol. This polymer mixture is sprayed onto the tablets in a conventional pan coater to obtain film-coated tablets which membrane coating weighs approximately 26.0 mg. A 0.50-mm hole is drilled through the coating in one face of the tablet.

A second composition is prepared by mixing 1.95 g of copolyvidone, 1.75 g of titanium dioxide, 6.25 g of Talc and 50.0 mg of Aluminium Lake Pouceau Red in isopropyl alcohol. This polymer mixture is sprayed onto the tablets in a conventional pan coater to obtain film-coated tablets which membrane coating weighs approximately 10 mg.

A third composition is prepared by mixing 10.0 g of loratadine, 90.91 g of microcrystalline cellulose, 89.55 g of lactose monohydrate, 17.27 g of corn starch, and 15.9 g povidone to form a mixture. The mixture is wet with a blend of 73.0 ml of purified water, 4.55 g of PEG 400 and 18.18 g of PEG 6000 to form a blend. The blend is granulated and dried at 40–50° C. for 2 hours. It is then mixed with 0.91 g of colloidal silicon dioxide. The mixture is blended to homogeneity. Then, 2.73 g of magnesium stearate is added as lubricant. This blend is compressed over the film-coated tablets using biconcaves, 10.0-mm diameter punches. Coating weight: 250 mg. Hardness from 7 to 12 kP.

A fourth composition to cover the third composition is prepared as follows: 14.25 g of cellulose acetate and 0.75 g of polyethylene glycol 400 in a mixture of 250 ml of acetone and 150 ml of methyl alcohol. This polymer mixture is sprayed onto the tablets in a conventional pan coater to obtain film-coated tablets which membrane coating weighs approximately 15.0 mg. A 0.50-mm hole is drilled through the coating on the same face of the tablet as the first hole.

The final coating is prepared by mixing 12.1 g of hydroxypropyl methylcellulose 2910, 3.42 g of polyethylene glycol 6000 and 4.48 g of titanium dioxide in a mixture of methylene chloride-alcohol 96° 70:30 v/v (volume/volume). This polymer mixture is sprayed onto the second semipermeable membrane (the fourth composition) of the tablets in a conventional pan coater to obtain film-coated tablets which membrane coating weighed approximately 20 mg.

An osmotic device prepared according to this example will provide a controlled release of montelukast (up to 100% released) over a period of about 18–24 hours (or throughout the period of 2–24 hours after administration) and a controlled release of loratadine (up to 100% released) over the period of 0–8 hours after administration. The release of montelukast begins about 2 hours after administration and ends about 18–24 hours after administration. The release of loratadine begins shortly after administration and end about 7–9 hours after administration.

EXAMPLE 2

A large scale batch of tramadol (400 mg strength) and rofecoxib (25 mg strength) tablets is prepared by mixing 400.0 g of tramadol, 26.67 g of mannitol, 69.0 g of microcrystalline cellulose and 12.67 g of povidone to form a mixture. The mixture is wet with a blend of 110.00 ml of alcohol 96°, 7.33 g of PEG 6000 to form a blend. The blend is granulated and dried at 40–50° C. for 3 hours; then, it is screened and mixed with 4.80 g of colloidal silicon dioxide. The blend is mixed to homogeneity and 2.70 g of magnesium stearate is added as lubricant. The final blend is tabletted using biconcaves, 10.0 mm diameter punches. Core weight: 525.0 mg. Hardness from 8–14 kP.

A first composition to cover the cores is prepared as follows: 38.0 g of cellulose acetate and 2.0 g of polyethylene glycol 400 in a mixture of 710 ml of acetone and 290 ml of methyl alcohol. This polymer mixture is sprayed onto the tablets in a conventional pan coater to obtain film-coated tablets which membrane coating weighs approximately 40.0 mg. A 0.50-mm hole is drilled through the coating in one face of the tablet.

A second composition is prepared by mixing 3.9 g of copolyvidone, 3.5 g of titanium dioxide, 12.5 g of Talc and 100.0 mg of Aluminum Lake Ponceau Red in isopropyl alcohol. This polymer mixture is sprayed onto the first semipermeable membrane (first composition) of the tablets in a conventional pan coater to obtain film-coated tablets which membrane coating weighs approximately 20 mg.

A third composition is prepared by mixing 25.00 g of rofecoxib, 289.0 g of microcrystalline cellulose, 86.0 g of sodium chloride, 65.0 g of PEO, 5.30 g of HPMC 2208 and 20.0 g povidone to form a mixture. The mixture is wet with a blend of 80.0 ml of alcohol 96° and 1.40 g of polysorbate 20 to form a blend. The blend is granulated and dried at 40–50° C. for 3 hours. It is then screened and mixed with 3.8 g of colloidal silicon dioxide. The mixture is blended to homogeneity. Then, 4.5 g of magnesium stearate is added as lubricant. This blend is compressed over the film-coated tablets using biconcaves, 14.0-mm diameter punches. Coating weight: 500 mg. Hardness from 6 to 10 kP.

A fourth composition to cover the third composition is prepared as follows: 19.0 g of cellulose acetate and 1.00 g of polyethylene glycol 400 is placed in a mixture of 350 ml of acetone and 150 ml of methyl alcohol. This polymer mixture is sprayed onto the tablets in a conventional pan coater to obtain film-coated tablets which membrane coating weighs approximately 20.0 mg. A 0.50-mm hole is drilled through the coating on the opposite face of the tablet as the first hole.

The final coating is prepared by mixing 12.1 g of hydroxypropyl methylcellulose 2910, 4.48 g of polyethylene glycol 6000 and 4.48 g of titanium dioxide in a mixture of methylene chloride-alcohol 96° 70:30 v/v (volume/volume). This polymer mixture is sprayed onto the second semipermeable membrane (the fourth composition) of the tablets in a conventional pan coater to obtain film-coated tablets which membrane coating weighs approximately 20 mg.

An osmotic device prepared according to this example will provide a controlled release of tramadol (up to 100% released) over a period of about 18–24 hours (or throughout the period of 3–24 hours after administration) and a controlled release of rofecoxib (up to 100% released) over the period of 0–16 hours after administration. The release of tramadol begins about 3 hours after administration and ends about 18–24 hours after administration. The release of rofecoxib begins shortly after administration and end about 14–18 hours after administration.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

We claim the following:

1. A dual osmotic device comprising a first osmotic device enclosed within a second osmotic device, wherein:

the first osmotic device comprises an active agent-containing composition enclosed within a first semipermeable membrane having at least one passageway for release of active agent from the core; and the second osmotic device comprises an active agent-containing composition enclosing the first semipermeable membrane and being enclosed within a second semipermeable membrane having at least one passageway for release of active agent from the dual osmotic device.

2. A dual osmotic device according to claim 1, wherein the first osmotic device comprises:
  a core comprising a first active agent, at least one excipient and a first osmagent;
  a first semipermeable membrane surrounding the core; and
  at least one first passageway in the first semipermeable membrane.

3. A dual osmotic device according to claim 2, wherein the second osmotic device comprises:
  an active agent coat surrounding the first semipermeable membrane and comprising a second active agent, at least one excipient and a second osmagent;
  a second semipermeable membrane surrounding the active agent coat; and
  at least one second passageway in the active agent coat.

4. A dual osmotic device according to claim 1, wherein the second semipermeable membrane loses its physical integrity during use.

5. A dual osmotic device according to claim 1, wherein the first and second active agents are different.

6. A dual osmotic device according to claim 1, wherein the first and second active agents are the same.

7. A dual osmotic device according to claim 4, wherein the second semipermeable membrane loses its physical integrity within about 3–30 hours after administration.

8. A dual osmotic device according to claim 7, wherein the first semipermeable membrane loses its physical integrity within about 24–31 hours after administration.

9. A dual osmotic device according to claim 1, wherein the second osmotic device delivers a majority of the second active agent by about 3–20 hours after exposure to an environment of use.

10. A dual osmotic device according to claim 1, wherein the first osmotic device delivers a majority of the first active agent by about 3–24 hours after exposure to an environment of use.

11. A dual osmotic device according to claim 1, wherein the second active agent is delivered to the upper to middle GI tract and first active agent is delivered to the middle to lower GI tract of a mammal to which the dual osmotic device is administered.

12. A dual osmotic device according to claim 1, wherein the first osmotic device provides a controlled delivery of the first active agent and the second osmotic device provides a controlled delivery of the second active agent.

13. A dual osmotic device according to claim 1, wherein the first and second active agents are delivered sequentially.

14. A dual osmotic device according to claim 1, wherein the first and second active agents are delivered in an overlapping manner.

15. A dual osmotic device according to claim 1 further comprising a water soluble or erodible coat between the first semipermeable membrane and the active agent coat.

16. A dual osmotic device according to claim 15, wherein the water soluble or erodible coat is selected from the group consisting of an inert coat, an enteric coat, a drug release-controlling coat, and a microporous coat.

17. A dual osmotic device according to claim 1 further comprising a water soluble or erodible coat between the first osmotic device and the second osmotic device.

18. A dual osmotic device according to claim 17 further comprising a rapid release active agent-containing coat external to the second osmotic device and comprising a third active agent that is released rapidly when the dual osmotic device is placed in an environment of use.

19. A dual osmotic device according to claim 18, wherein at least two of the first, second and third active agents are different.

20. A dual osmotic device according to any one of claims 1, 3, 4, 7, 9, 11, 13, 14, 15, 17, or 18 wherein the active agents are independently selected at each occurrence from the group consisting of a biologically or pharmacologically active agent, medicine, nutrient, food product, insecticide, pesticide, herbicide, germicide, algaecide, fungicide, chemical reagent, growth regulating substance, parasiticide, sex sterilant, fertility promotor, biocide, rodenticide, disinfectant, antioxidant, plant growth promotor, preservative, fermentation agent, fertility inhibitor, deodorant, microorganism attenuator, catalyst, food supplement, cosmetic, and vitamin.

21. An active agent delivery device comprising:
  a first osmotic device comprising a core comprising a first active agent, at least one pharmaceutical excipient and a first osmagent; a first semipermeable membrane surrounding the core; and at least one first passageway in the first semipermeable membrane; and
  a second osmotic device enclosing the first osmotic device and comprising an active agent coat surrounding the first semipermeable membrane and comprising a second active agent, at least one pharmaceutical excipient and a second osmagent; a second semipermeable membrane surrounding the active agent coat; and at least one second passageway in the second semipermeable membrane.

22. An active agent delivery device according to claim 21 further comprising a water soluble or erodible coat between the first semipermeable membrane and the active agent coat.

23. An active agent delivery device according to claim 22, wherein the water soluble or erodible coat is selected from the group consisting of an inert coat, an enteric coat, a drug release-controlling coat, and a microporous coat.

24. An active agent delivery device according to claim 21, wherein at least one of the first and second semipermeable membranes loses its physical integrity during use.

25. An active agent delivery device according to claim 21 further comprising a rapid release active agent-containing coat external to the second osmotic device, wherein the rapid release active agent-containing coat comprises a third active agent that is released rapidly when the dual osmotic device is placed in an environment of use.

26. An active agent delivery device according to claim 25, wherein at least two of the first active agent, second active agent and third active agent are different.

27. An active agent delivery device according to claim 21, wherein the second osmotic device delivers a majority of the second active agent by about 3–20 hours after exposure to an aqueous environment of use.

28. An active agent delivery device according to claim 21, wherein the active agent is independently selected at each occurrence from the group consisting of an antibiotic, antihistamine, decongestant, antiinflammatory agent, antiparasitic agent, antiviral agent, local anesthetic, antifungal agent, amoebicidal agent, trichomonocidal agent, analgesic agent, antiarthritis agent, anthiasthmatic, anticoagulant, anticonvulsant agent, antidepressant agent, antidiabetic agent, antineoplastic agent, antipsychotic agent, neuroleptic agent, antihypertensive agent, antidepressant agent, hypnotic agent, sedative, anxyolitic energizer, anti-convulsant agent, antiparkinson agent, muscle relaxant, antimalarial agent, hormonal agent, contraceptive, sympathomimetic agent, diuretic, hypoglycemic agent, ophthalmic agent, electrolyte, diagnostic agent and cardiovascular agent.

29. An active agent delivery device according to claim 27, wherein the first osmotic device delivers a majority of the first active agent after about 3–24 hours after exposure to an aqueous environment of use.

30. A dual osmotic device comprising:
a first osmotic device comprising a first active agent-containing composition enclosed within a first membrane having at least one passageway there through; and
a second osmotic device comprising a second active agent-containing composition enclosing the first membrane and being enclosed within a second membrane having at least one passageway there through;
wherein the first and second active agents are released in a controlled manner.

31. The dual osmotic device of claim 30, wherein the active agent is independently selected at each occurrence from the group consisting of a biologically or pharmacologically active agent, medicine, nutrient, food product, insecticide, pesticide, herbicide, germicide, algaecide, fungicide, chemical reagent, growth regulating substance, parasiticide, sex sterilant, fertility promoter, biocide, rodenticide, disinfectant, antioxidant, plant growth promoter, preservative, fermentation agent, fertility inhibitor, deodorant, microorganism attenuator, catalyst, food supplement, cosmetic, and vitamin.

32. The dual osmotic device of claim 30, wherein the first and/or second membrane loses its physical integrity during use of the dual osmotic device.

33. The dual osmotic device of claim 30, wherein the second osmotic device delivers a majority of the second active agent by about 3–20 hours after exposure to an environment of use.

34. The dual osmotic device of claim 30, wherein the first osmotic device delivers a majority of the first active agent by about 3–24 hours after exposure to an environment of use.

35. The dual osmotic device of claim 30, wherein the first and second active agents are delivered sequentially.

36. The dual osmotic device of claim 35, wherein the second active agent is delivered to the upper to middle GI tract and first active agent is delivered to the middle to lower GI tract of a mammal to which the dual osmotic device is administered.

37. The dual osmotic device of claim 30, wherein the first and second active agents are delivered in an overlapping manner.

38. The dual osmotic device of claim 30 further comprising a water soluble or erodible coat between the first osmotic device and the second osmotic device.

39. The dual osmotic device of claim 38, wherein the water soluble or erodible coat is selected from the group consisting of an inert coat, an enteric coat, a drug release-controlling coat, and a microporous coat.

40. The dual osmotic device of claim 30 further comprising a rapid release active agent-containing coat external to the second osmotic device and comprising a third active agent that is released rapidly when the dual osmotic device is placed in an environment of use.

41. The dual osmotic device of claim 40, wherein at least two of the first, second and third active agents are different.

42. The dual osmotic device of claim 30 further comprising a water soluble or erodible coat between the first osmotic device and the second osmotic device, and a rapid release active agent-containing coat external to the second osmotic device and comprising a third active agent that is released rapidly when the dual osmotic device is placed in an environment of use; wherein the first and second active agents are delivered sequentially.

43. The dual osmotic device of claim 42, wherein the first and/or second membrane loses its physical integrity during use of the dual osmotic device.

44. The dual osmotic device of claim 42, wherein the second osmotic device delivers a majority of the second active agent by about 3–20 hours after exposure to an environment of use.

45. The dual osmotic device of claim 42, wherein the first osmotic device delivers a majority of the second active agent by about 3–24 hours after exposure to an environment of use.

46. The dual osmotic device of claim 42, wherein the water soluble or erodible coat is selected from the group consisting of an inert coat, an enteric coat, a drug release-controlling coat, and a microporous coat.

47. The dual osmotic device of claim 42, wherein the second active agent is delivered to the upper to middle GI tract and first active agent is delivered to the middle to lower GI tract of a mammal to which the dual osmotic device is administered.

48. The dual osmotic device of claim 30, 32, 35, 37–40, 42–43, 46 or 47, wherein the active agent is independently selected at each occurrence from the group consisting of an antibiotic, antihistamine, decongestant, antiinflammatory agent, antiparasitic agent, antiviral agent, local anesthetic, antifungal agent, amoebicidal agent, trichomonocidal agent, analgesic agent, antiarthritis agent, anthiasthmatic, anticoagulant, anticonvulsant agent, antidepressant agent, antidiabetic agent, antineoplastic agent, antipsychotic agent, neuroleptic agent, antihypertensive agent, antidepressant agent, hypnotic agent, sedative, anxyolitic energizer, anticonvulsant agent, antiparkinson agent, muscle relaxant, antimalarial agent, hormonal agent, contraceptive, sympathomimetic agent, diuretic, hypoglycemic agent, ophthalmic agent, electrolyte, diagnostic agent and cardiovascular agent.

49. The active agent delivery device of claim 21–24 or 25, wherein the active agent is independently selected at each occurrence from the group consisting of a biologically or pharmacologically active agent, medicine, nutrient, food product, insecticide, pesticide, herbicide, germicide, algaecide, fungicide, chemical reagent, growth regulating substance, parasiticide, sex sterilant, fertility promoter, biocide, rodenticide, disinfectant, antioxidant, plant growth promoter, preservative, fermentation agent, fertility inhibitor, deodorant, microorganism attenuator, catalyst, food supplement, cosmetic, and vitamin.

50. The dual osmotic device of claim 17 or 38, wherein the first active agent is an anti-asthmatic agent and the second active agent is an antihistamine.

51. The dual osmotic device of claim 50, wherein the anti-asthmatic agent is a leukotriene inhibitor and the antihistamine is an antihistamine H1 antagonist.

52. The dual osmotic device of claim 50, wherein the anti-asthmatic agent is selected from the group consisting of theophylline, beclomethasone dipropionate, budesonide, flunisolide, prednisone, albuterol, salbutamol, salmetherol, terbutaline, ipratopium bromide, cromolyn sodium and montelukast, and the antihistamine is selected from the group consisting of diphenhydramine, pirilamine, chlorpheniramine, brompheniramine, promethazine, astemizole, loratadine and terfenadine.

53. The dual osmotic device of claim 17 or 38, wherein the first active agent is a first analgesic agent and the second active agent is different second analgesic agent.

54. The dual osmotic device of claim 53, wherein the first and second analgesic agents are independently selected from the group consisting of tramadol, rofecoxib, cortisone, hydrocortisone, prednisone, prednisolone, betamethasone, dexamethasone, fluorocortisone, salicylic acid, aspirin, diflunisal, phenylbutazone, oxyphenbutazone, dipyrone, acetaminophen, phenacetin, indomethacin, sulindac, mefenamic acid, tolmetin, ibuprofen, naproxen, fenoprofen, ketoprofen, flurbiprofen, indoprofen, piroxicam, diclofenac, morphine, codeine, meperidine and nalorphine.

55. The dual osmotic device of claim 53, wherein the first analgesic agent is an opioid analgesic and the second analgesic agent is a cyclooxygenase-II inhibitor.

* * * * *